United States Patent
Gounis et al.

(10) Patent No.: US 10,092,252 B2
(45) Date of Patent: Oct. 9, 2018

(54) VASCULAR PHANTOMS AND METHOD OF MAKING SAME

(71) Applicants: Matthew J. Gounis, Shrewsbury, MA (US); Juyu Chueh, Clinton, MA (US)

(72) Inventors: Matthew J. Gounis, Shrewsbury, MA (US); Juyu Chueh, Clinton, MA (US)

(73) Assignee: University of Massachusetts, Boston, MA (US)

( * ) Notice: Subject to any disclaimer, the term of this patent is extended or adjusted under 35 U.S.C. 154(b) by 312 days.

(21) Appl. No.: 14/680,506

(22) Filed: Apr. 7, 2015

(65) Prior Publication Data

US 2015/0282963 A1 Oct. 8, 2015

Related U.S. Application Data

(60) Provisional application No. 61/976,172, filed on Apr. 7, 2014.

(51) Int. Cl.
| | |
|---|---|
| *B29C 39/10* | (2006.01) |
| *A61B 6/03* | (2006.01) |
| *B29C 39/00* | (2006.01) |
| *B29C 39/02* | (2006.01) |
| *B29C 39/12* | (2006.01) |
| *B29C 39/36* | (2006.01) |
| *A61B 5/055* | (2006.01) |
| *B29L 31/00* | (2006.01) |
| *A61B 5/02* | (2006.01) |
| *A61B 6/00* | (2006.01) |
| *A61B 34/10* | (2016.01) |

(52) U.S. Cl.
CPC ............ *A61B 6/032* (2013.01); *A61B 5/055* (2013.01); *B29C 39/003* (2013.01); *B29C 39/021* (2013.01); *B29C 39/026* (2013.01); *B29C 39/10* (2013.01); *B29C 39/12* (2013.01); *B29C 39/36* (2013.01); *A61B 5/02007* (2013.01); *A61B 6/03* (2013.01); *A61B 6/504* (2013.01); *A61B 6/583* (2013.01); *A61B 2034/105* (2016.02); *A61F 2240/001* (2013.01); *B29L 2031/753* (2013.01)

(58) Field of Classification Search
CPC ........... A61F 2240/001; B29C 33/3842; B29C 39/10
See application file for complete search history.

(56) References Cited

U.S. PATENT DOCUMENTS

2014/0260524 A1* 9/2014 Seo .................. G01N 29/30
73/1.86

OTHER PUBLICATIONS

Chueh J.Y., Wakhloo A.K.and Gounis M.J., "Neurovascular Modeling: Small-Batch Manufacturing of Silicone Vascular Replicas," AJNR Am J Neuroradiol Jun. 2009 30: 1159-1164.*

* cited by examiner

*Primary Examiner* — James Sanders
(74) *Attorney, Agent, or Firm* — Milstein Zhang & Wu LLC

(57) ABSTRACT

A method of making a vascular phantom based on imaging data of vasculature of a subject. A mold having a core and a shell is constructed based on the imaging data. A liquid precursor is introduced into the mold and is cured. The mold is removed, leaving a model of the vasculature of the subject. A plaque component is fabricated by making a plaque mold and introducing liquid precursors containing T1 and T2 modifiers to mimic the T1 and T2 of portions of the plaque. The plaque components are attached to the vasculature using adhesive.

5 Claims, 5 Drawing Sheets

VASCULAR PHANTOMS AND METHOD OF MAKING SAME

CROSS-REFERENCE TO RELATED APPLICATIONS

This application claims priority to and the benefit of U.S. provisional patent application Ser. No. 61/976,172, filed Apr. 7, 2014, which application is incorporated herein by reference in its entirety.

FIELD OF THE INVENTION

The invention relates to modeling or imaging vascular systems in general and particularly to methods of making and using vascular phantoms.

THE NAMES OF THE PARTIES TO A JOINT RESEARCH AGREEMENT

The parties involved in a joint research agreement include the inventors of this application (Matthew Gounis and Juyu Chueh of University of Massachusetts Medical School) and Tanya N. Turan M. D. (Medical University of South Carolina) Truman R. Brown, Ph.D. (Medical University of South Carolina) Richard Swartz M D, PhD, FRCPC (University of Toronto), and Edward Feldmann, M D (Tufts Medical Center).

BACKGROUND OF THE INVENTION

Intracranial atherosclerotic disease (ICAD) is the most common cause of stroke throughout the world. Patients with severe arterial stenosis and a recent stroke or transient ischemic attack are at high risk of recurring stroke. In an attempt to improve the clinical outcome of patients with severe, symptomatic ICAD, percutaneous transluminal angioplasty and stenting have become treatment options over the last years. The SAMMPRIS trial has shown that endovascular treatment does not have favorable outcomes when compared to aggressive medical management. See Chimowitz M, Lynn M, Derdeyn C, et al. Stenting versus aggressive medical therapy for intracranial arterial stenosis. N Engl J Med. 2011;365(11):993-1003. However, patient inclusion of this trial was based on angiographically verified stenosis and did not include a determination of the components of the stenotic plaque, which may be a cause for bias.

Although catheter angiography is currently the gold standard imaging technique for ICAD, it is an invasive procedure that conveys a significant risk of morbidity and mortality. In addition, this technique merely demonstrates vessel narrowing and does not provide characteristics of the atherosclerotic plaque, nor information about the vessel wall or the underlying etiology. With less invasive angiography methods such as MRA and CTA, the degree of stenosis is not always fully appreciated and may not disclose the underlying source. See Feldmann E, Wilterdink J, Kosinski A, et al. The stroke outcomes and neuroimaging of intracranial atherosclerosis (SONIA) trial. Neurology. 2007;68(24):2099-2106.

High resolution vessel wall MRI has shown to be an excellent technique to differentiate between the various pathologies that may be the cause of the stenosis and even allow characterization of plaque composition. See Xu W H, Li M L, Gao S, et al. In vivo high-resolution MR imaging of symptomatic and asymptomatic middle cerebral artery atherosclerotic stenosis. Atherosclerosis. 2010; 212(2):507-511; van der Kolk A G, Zwanenburg J J M, Brundel M, et al. Intracranial vessel wall imaging at 7.0-T MRI. Stroke. 2011; 42(9):2478-2484; Swartz R, Bhuta S, Farb R, et al. Intracranial arterial wall imaging using high-resolution 3-tesla contrast-enhanced MRI. Neurology. 2009; 72(7):627-634; Skarpathiotakis M, Mandell D, Swartz R, Tomlinson G, Mikulis D. Intracranial atherosclerotic plaque enhancement in patients with ischemic stroke. AJNR Am JNeuroradiol. 2012; Qiao Y, Steinman D A, Qin Q, et al. Intracranial arterial wall imaging using three-dimensional high isotropic resolution black blood MRI at 3.0 Tesla. JMRI J Magn Reson Im. 2011; 34(1):22-30; Mandell D M, Matouk C C, Farb R I, et al. Vessel wall MRI to differentiate between reversible cerebral vasoconstriction syndrome and central nervous system vasculitis preliminary results. Stroke. 2012; 43 (3):860-862; and Li M, Xu W, Song L, et al. Atherosclerosis of middle cerebral artery: evaluation with high-resolution MR imaging at 3T. Atherosclerosis. 2009; 204(2): 447-452.

Various vessel wall imaging sequences have been proposed to use different techniques to suppress the signal of blood and obtain high resolution image data. However, a standard of reference to quantify their sensitivity and specificity is currently not available. See Degnan A, Gallagher G, Teng Z, Lu J, Liu Q, Gillard J. MR angiography and imaging for the evaluation of middle cerebral artery atherosclerotic disease. AJNR Am JNeuroradiol. 2012; 33(8):1427-1435.

Several different manufacturing processes of vascular replicas have been demonstrated in previous studies. The patient-specific vasculature models were first obtained either by injecting methylmethacrylate into the human cadavers to get vascular lumen casts of the part of interest or sending data derived from images generated from the imaging facilities to 3D printer for rapid prototyping. In the former method, postmortem alterations, including the shrinkage of arterial trees, produced dimensional errors of the in vitro model. Different methods including repeated painting, dip-spin processing, and lost-wax technique were then applied to the casts to form the elastomeric replicas. The repeated panting and dip-spin procedure was time-consuming and not reproducible. On the other hand, the major concern of lost-wax technique was the fragility of the wax, which resulted in the breakage of the vessel branches smaller than 1 mm.

References to the prior art include Ikeda S, Arai F, Fukuda T, et al. An in vitro patient-tailored model of human cerebral artery for simulating endovascular intervention. Med Image Comput Comput Assist Intery Int Conf Med Image Comput Comput Assist Intery 2005; 8:925-32; Suzuki Y, Fujitsuka M, Chaloupka J C. Simulation of endovascular neurointervention using silicone models: imaging and manipulation. Neurol Med Chir (Tokyo) 2005; 45:567-72, discussion 572-73; Gruber A, Bavinszki G, Killer M, et al. In vitro training model for endovascular embolization of cerebral aneurysms. Minim Invasive Neurosurg 1997; 40:121-23; Barath K, Cassot F, Rufenacht D A, et al. Anatomically shaped internal carotid artery aneurysm in vitro model for flow analysis to evaluate stent effect. AJNR Am J Neuroradiol 2004; 25:1750-59; Cortez M A, Quintana R, Wicker R B. Multistep dip-spin coating manufacturing system for silicone cardiovascular membrane fabrication with prescribed compliance. Int J Adv Manuf Technol 2006;34:667-79; Gailloud P, Pray J R, Muster M, et al. An in vitro anatomic model of the human cerebral arteries with saccular arterial aneurysms. Surg Radiol Anat 1997; 19:119-21; Knox K, Kerber C W, Singel S A, et al. Rapid prototyping to create vascular replicas from CT scan data: making tools to teach, rehearse, and choose treatment strategies. Catheter Cardiovasc Interv 2005; 65:47-53; Markl M, Schumacher R, Kuffer J, et al. Rapid vessel prototyping: vascular modeling using 3T magnetic resonance angiography and rapid prototyping technology. MAGMA 2005; 18:288-92; Seong J, Sadasivan C, Onizuka M, et al. Morphology of elastase-induced cerebral aneurysm model in rabbit and rapid prototyping of elastomeric transparent replicas. Biorheology 2005;42:345-61; Sugiu K, Martin J B, Jean B, et al. Artificial cerebral aneurysm model for med medical testing, training, and research. Neurol Med Chir (Tokyo) 2003; 43:69-72, discussion 73; Wetzel S G, Ohta M, Handa A, et al. From patient to model: stereolithographic modeling of the cerebral vasculature based on rotational angiography. AJNR Am J Neuroradiol 2005; 26:1425-27; and Ohta M, Handa A, Iwata H, et al. Poly-vinyl alcohol hydrogel vascular models for in vitro aneurysm simulations: the key to low friction surfaces. Technol Health Care 2004; 12:225-33.

Silicone elastomer is frequently used for preparation of vascular replicas. However, silicone elastomer has a high friction coefficient and is tacky which can make advance of endovascular devices difficult. To date, polyvinyl alcohol (PVA) is used as an alternative material to construct vascular replicas in the application of neurovascular modeling. The high water content of PVA hydrogel not only gives vascular replicas a naturally lubricated surface but also provides good visibility.

There is a need for improved methods of imaging or modeling vascular systems so that more effective treatment may be provided to patients.

SUMMARY OF THE INVENTION

In a previous publication, J. Y. Chueh, A. K. Wakhloo and M. J. Gounis, "Neurovascular Modeling: Small-Batch Manufacturing of Silicone Vascular Replicas," AJNR Am J Neuroradiol June 2009 30: 1159-1164, we described how a vascular replica was constructed using a model comprising a solid core and a shell made from ABS (a copolymer of acrylonitrile, butadiene and styrene) in which silicone (Sylgard 184 silicone, or LIM 6030) was injected, and the core and shell dissolved using xylene.

We now describe several improvements that we have invented for making such vascular replicas or vascular phantoms.

According to one aspect, the invention features a method of fabricating a vascular phantom from imaging data of vasculature of a subject. The method comprises the steps of: forming a core-shell mold having a core and an outer shell with dimensions based on the imaging data of the vasculature of the subject; infusing the core-shell mold with a liquid precursor; curing the liquid precursor; and dissolving the core-shell mold to recover a vascular phantom that represents the vasculature of the subject.

In another embodiment, the core-shell mold is fabricated using three dimensional printing.

In yet another embodiment, the method further comprises the steps of: forming a plaque mold having dimensions based on the imaging data of the vasculature of the subject; filling the plaque mold with a gel-like plaque component; freezing the plaque component; removing the plaque component from the plaque mold; and attaching the plaque component to the vascular phantom that represents the vasculature of the subject. The gel-like material can comprise T1 and T2 modifiers, water, agarose, and carrageenan. By adjusting the ratio of T1 and T2 modifiers one can prepare materials with different T1 and T2 characteristics, mimicking a hemorrhage, a lipid core, or a fibrous cap.

In still another embodiment, the plaque represents one or more of a hemorrhage, a lipid core, and a fibrous cap.

In a further embodiment, one or more of the hemorrhage, the lipid core, and the fibrous cap comprises respective amounts of a T1 modifier and a T2 modifier. The MRI signal properties such as the T1 and T2 of the phantom will be similar to those of the clinical specimens.

In yet a further embodiment, the step of attaching the plaque to the vascular phantom includes by coating a layer of adhesive on one or both of the shaped plaque and the vascular replica and performing a curing process.

In an additional embodiment, the core-shell mold includes a hollow core.

In one more embodiment, the core-shell mold includes support material between the core and the outer shell.

In still a further embodiment, the liquid precursor is PVA.

In yet a further embodiment, the liquid precursor is a mixture of PVA and gelatin.

In one embodiment, the liquid precursor is silicone.

In a further embodiment, the step of dissolving the core-shell mold is performed using xylene.

According to another aspect, the invention relates to a vascular phantom, comprising: a liquid precursor configured to be infused into a core-shell mold having a core and an outer shell with dimensions based on imaging data of a vasculature of a subject, the liquid precursor configured to be cured, and the liquid precursor configured to constitute a recovered vascular phantom after the core-shell mold is dissolved.

According to a further aspect, the invention relates to a method of using a vascular phantom. The method comprises the steps of: obtaining imaging data on a vasculature of a living subject; forming a core-shell mold having a core and an outer shell with dimensions based on the imaging data of the vasculature of the living subject; infusing the core-shell mold with a liquid precursor; curing the liquid precursor; dissolving the core-shell mold to recover a vascular phantom that represents the vasculature of the living subject; and performing a medical procedure on the vascular phantom as a trial procedure prior to performing the medical procedure on the living subject.

In one embodiment, the method of using a vascular phantom further comprises the step of determining that the medical procedure is appropriate for use on the living subject.

In another embodiment, the method of using a vascular phantom further comprises the step of performing the medical procedure on the living subject.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION

Currently, there is no standard protocol for MR-imaging of ICAD, nor a gold standard phantom to compare MR-sequences. In addition, MRI scanners produced by different vendors will have different sequences for ICAD imaging. The present invention provides a platform for establishing a uniform imaging method for diagnosis of ICAD.

In a first embodiment, one can prepare a vascular replica of atherosclerotic plaque which comprises a stenosed vessel lumen and intracranial atherosclerotic plaque components, including a lipid core, a hemorrhage, and a fibrous cap constructed for MR imaging.

In order to overcome the aforesaid limitations, a small batch manufacturing process has been employed to construct the stenosed vessel lumen. Clinical imaging data such as CT or MRI of patients with atherosclerotic plaques can be used for 3D reconstruction of cerebrovasculatures and each plaque component.

Figures 1A, 1B, 1C, 1D:
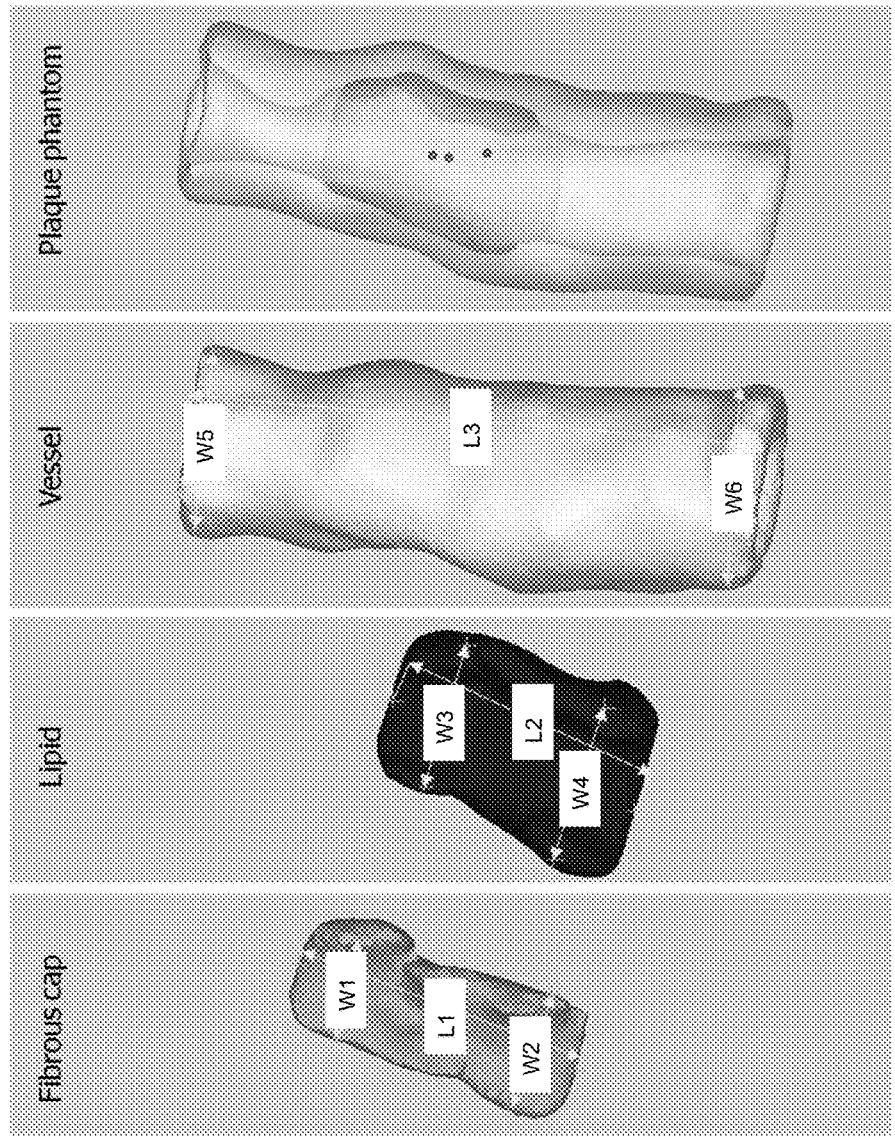
FIG. 1A is an image of the fibrous cap component of a stenosed vessel.
FIG. 1B is an image of the lipid component of a stenosed vessel.
FIG. 1C is an image of the vessel component of a stenosed vessel.
FIG. 1D is an image of the reconstructed stenosed vessel.

FIG. 1A is an image of the fibrous cap component of a stenosed vessel. In FIG. 1A width dimensions are shown as W1 and W2 and a length dimension is shown as L1.

FIG. 1B is an image of the lipid component of a stenosed vessel. In FIG. 1B width dimensions are shown as W3 and W4 and a length dimension is shown as L2.

FIG. 1C is an image of the vessel component of a stenosed vessel. In FIG. 1C width dimensions are shown as W5 and W6 and a length dimension is shown as L3.

The dimensions for one example are listed in Table 1.

TABLE 1

| Parameter | Value in millimeters |
| --- | --- |
| W1 | 2.960 |
| W2 | 3.395 |
| L1 | 8.814 |
| W3 | 4.345 |
| W4 | 4.489 |
| L2 | 7.116 |
| W5 | 6.120 |
| W6 | 7.045 |
| L3 | 20.042 |

FIG. 1D is an image of the reconstructed stenosed vessel.

Figure 2C:
FIG. 2C is an image of a hydrogel vascular replica of a stenosed vessel.
Figures 2A, 2B:
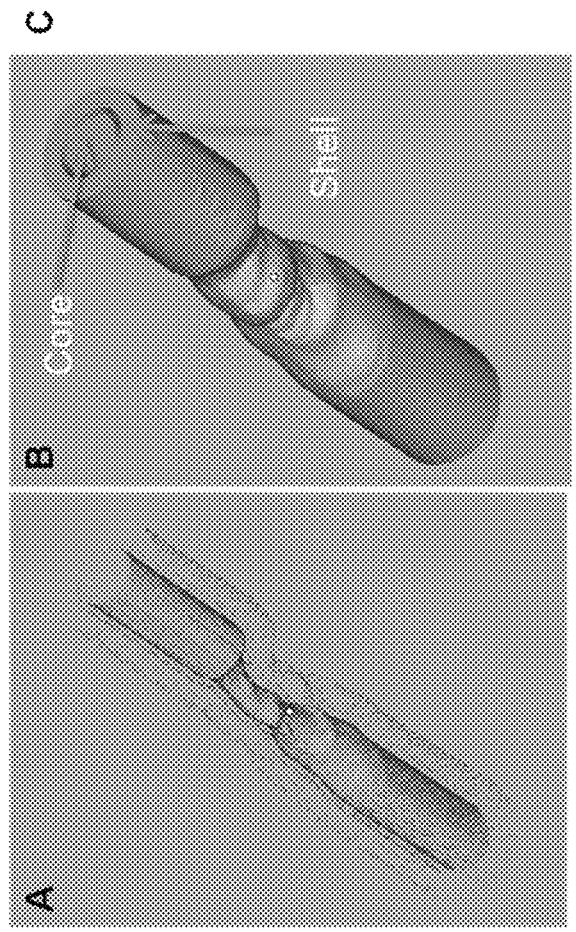
FIG. 2A is an image of a core in a core-shell model of a stenosed vessel.
FIG. 2B is an image of a shell with a core situated therein in a core-shell model of a stenosed vessel.

With the knowledge of the geometric parameters such as vessel diameter and length, a computer core-shell model can be designed, as illustrated in FIG. 2A and FIG. 2B. FIG. 2A is an image of a core in a core-shell model of a stenosed vessel. FIG. 2B is an image of a shell with a core situated therein in a core-shell model of a stenosed vessel.

The distance between the core and shell in FIG. 2B represents the thickness of the vascular replica, and can be precisely adjusted. A 3D printer converts the virtual design into a physical model by using the fused deposit manufacturing technique. Hydrogel is infused into the core-shell model by liquid injection molding and undergoes several freeze-thaw cycles for coagulation. The whole model is then immersed in xylene for complete mold dissolution, resulting in a hydrogel vascular replica as shown in FIG. 2C.

Three plaque models can be created including a hemorrhage, a lipid core, and a fibrous cap. Each component has different T1 and T2 values. Altering amounts of the T1 and T2 modifiers, gadolinium chloride and agarose, respectively, the plaque phantoms exhibit T1 and T2 times similar to the clinical values. In addition to the T1 and T2 modifiers, the plaque phantoms are comprised of carrageenan, sodium azide, water, and sodium chloride. To precisely control the volume of each plaque component, a plaque mold made of silicone with known shape and dimension can be built.

Figures 3A, 3B:
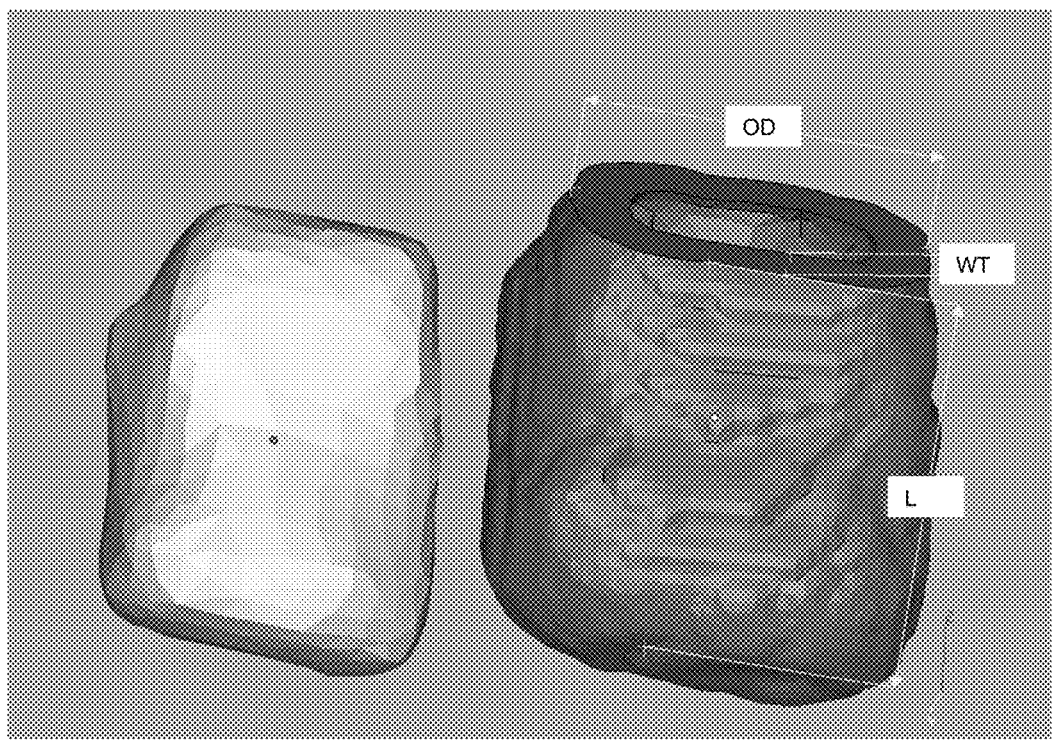
FIG. 3A is an image of a lipid core component constructed using a mixture of gadolinium chloride and agarose.
FIG. 3B is an image of a mold used to form the lipid core of FIG. 3A.

FIG. 3A is an image of a lipid core component constructed using a mixture of gadolinium chloride, agarose carrageenan, sodium azide, water, and sodium chloride.

FIG. 3B is an image of a plaque mold used to form the lipid core of FIG. 3A.

In FIG. 3B an outside dimension is shown as OD, a wall thickness dimension is shown as WT, and a length dimension is shown as L.

The dimensions for one example are listed in Table 2.

TABLE 2

| Parameter | Value in millimeters |
| --- | --- |
| OD | 5.861 |
| WT | 0.996 |
| L | 6.523 |

Each plaque component can be attached or glued to the vascular replica by using an adhesive such as polyvinyl alcohol. As a result, the replica can be used as a gold standard phantom for imaging of intracranial atherosclerotic disease on which MRI sequences, specifically developed to visualize intracranial plaque, can be evaluated by quantifiable metrics, such as volume and length measurements. The replica can be attached to a flow-loop filled with a blood mimicking fluid driven by a cardiac duplicator in order to optimize the signal suppression from blood flow.

In a second embodiment, one can construct a vascular model with complex and detailed structure for medical simulation and imaging by using a multi-step manufacturing process.

In this embodiment, a small batch manufacturing technique is provided to create cerebrovascular replicas that offer detailed geometry from clinical imaging data. The vascular replica also provides versatile applications such as surgical simulation, interventional practice, and hemodynamic research in vitro. To facilitate optical observation and simulate physiological environment, the replica is designed to be transparent and elastic with low friction, uniform thickness and good compatibility with imaging modalities such as computed tomography (CT), magnetic resonance imaging (MRI) and three-dimensional rotational angiography. The multi-step manufacturing process is described below.

Step 1—Preparation of a Core-Shell Mold

In the method of the present invention, different clinical imaging data such as CT or MRI of patients with or without pathologic findings can be used for 3D reconstruction of cerebrovasculatures. To prepare a diseased phantom such as the plaque model presented in FIG. 4, a stenosed vessel wall (401 in FIG. 4 and 501 FIG. 5) is used as the core to design and construct a layer of outer shell (502 in FIG. 5).

Figure 4:
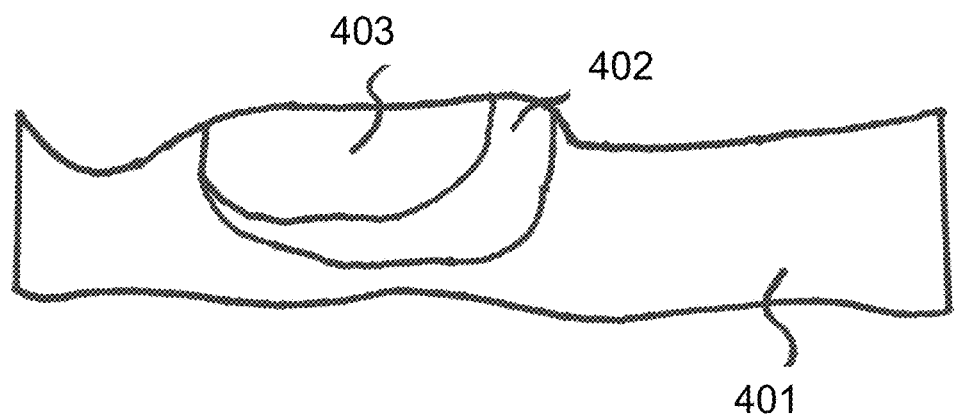
FIG. 4 shows a lateral view of an atherosclerotic plaque model.

FIG. 4 shows a lateral view of an atherosclerotic plaque model. In FIG. 4, 401 is a stenosed vessel lumen, 402 is a fibrous cap plaque component, and 403 is a lipid plaque component.

Figure 5:
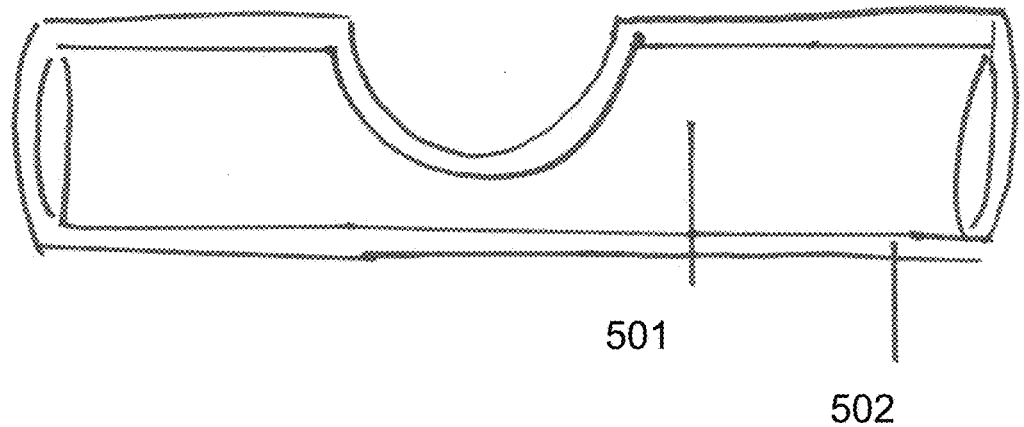
FIG. 5 shows a lateral view of a core-shell mold for PVA infusion.

FIG. 5 shows a lateral view of a core-shell mold for PVA infusion. In FIG. 5, 501 is a core of a stenosed vessel wall, and 502 is an outer shell.

Figure 6:
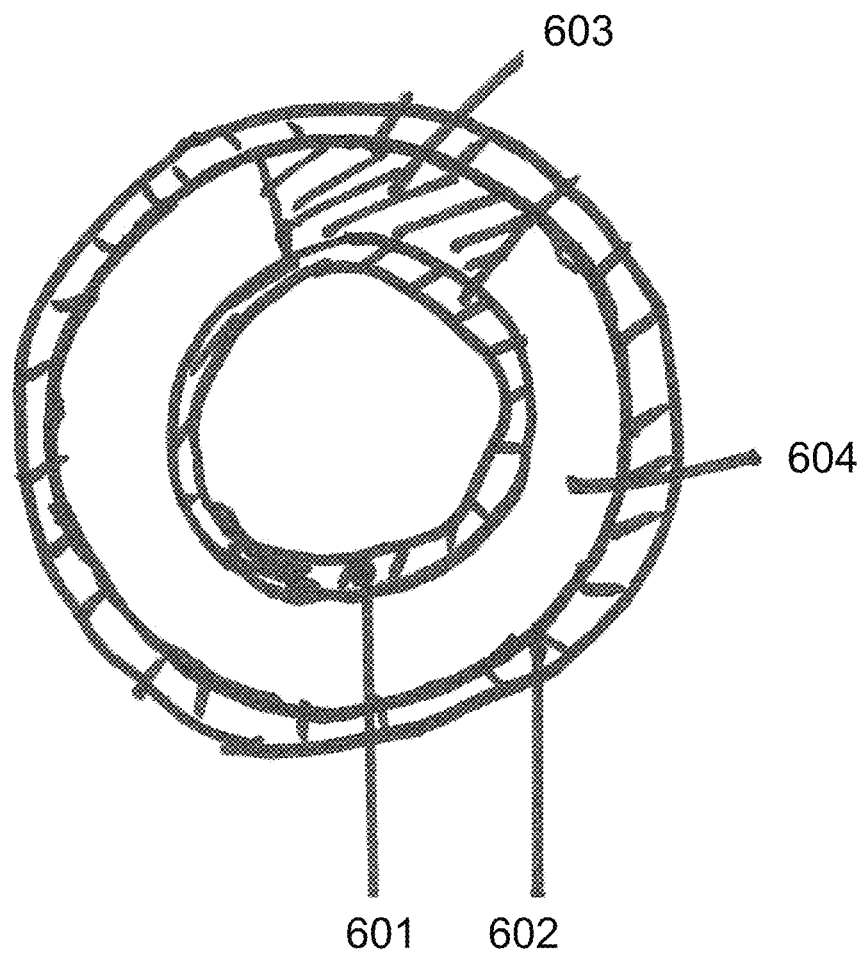
FIG. 6 shows a cross-section view of the core-shell model.

FIG. 6 shows a cross-section view of the core-shell model. In FIG. 6, 601 is a core of a stenosed vessel wall, 602 is an outer shell, 603 is support material, and 604 is empty space between core and shell for PVA infusion. Support material 603 is added between the core and the outer shell to prevent the outer shell from collapsing. The distance of empty space 604 between the core 601 and shell 602 represents the thickness of the vascular replica, which can be precisely controlled. The virtual design is converted into a physical model by using the fused deposit manufacturing technique or other 3D printing technologies as is convenient.

Step 2—Infusion of a Precursor

A precursor, for example a hydrogel such as polyvinyl alcohol (PVA) or a thermoplastic material, is infused into the core-shell model for example by liquid injection molding.

Step 3—Curing the Precursor to Form a Model Part

The infused core-shell model is subjected to one or more freeze-thaw cycles for curing. Preferably, more than one freeze-thaw cycle is performed. This forms the model part within the core-shell model.

Step 4—Dissolution or Removal of the Core-Shell Mold

In one embodiment, the whole model including the core-shell mold is immersed in a solvent, for example xylene, for mold dissolution.

One improvement provided by the second embodiment (the PVA model) is that it doesn't swell in xylene after removal of the outer shell as does the first embodiment (the silicone model).

In the second embodiment, it is also possible to modify the inner core 401, 501, 601. In a prior design the inner core was a solid piece. In the second embodiment, the inner core can be designed to have a hollow structure which allows xylene to flow into the mold and to quickly dissolve the tortuous inner core, such as 601. After removing the inner core, a transparent PVA vascular replica of a stenosed vessel wall is obtained.

The second embodiment is used to build a core-shell mold for each plaque component (402, 403 in FIG. 4). The core-shell molds for plaque components are filled with silicone (not PVA), and dissolved in xylene to yield "silicone containers" for lesion creation. Plaque component made of gelatin/gadolinium-based MRI contrast agent mixture is infused into the silicone container and set at −80° C. for 1 hour. The silicone container is carefully cut open to release the shaped plaque component. The shaped plaque component is then attached to the PVA vascular replica of a stenosed vessel wall by coating a layer of adhesive such as liquid PVA solution on one or both of the shaped plaque and the PVA vascular replica and performing a curing process.

The replica is useful for workers who wish to evaluate their MR-imaging setup/sequence for imaging of ICAD. The technique has larger implications for also medical device testing in realistic models of the human vasculature.

The present model is built from medical imaging data. The data can be data recorded from test subjects, or from medical subjects whose vasculature is the subject of interest. It is also possible to use synthetic data if one wants to generate a phantom for study under assumptions of some general medical condition of interest that is not specific to any one individual (e.g., how different amounts of plaque, or different locations where plaque is found might affect a specific situation).

The vascular phantoms of the invention can be used to perform a medical procedure on the vascular phantom as a trial procedure prior to performing the medical procedure on the living subject. This can allow a medical professional to gain a better understanding of how to carry out the proposed procedure on a specific living subject without subjecting that living subject to the hazards of an actual procedure, and then performing the procedure on the living subject after a determination is made that the proposed procedure is suitable for that living subject.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, patent application publication, journal article, book, published paper, or other publicly available material identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. A method of fabricating a vascular phantom from imaging data of vasculature of a subject, comprising the steps of: forming a core-shell mold having a core and an outer shell with dimensions based on the imaging data of the vasculature of the subject; infusing the core-shell mold with a liquid precursor; curing the liquid precursor; dissolving the core-shell mold to recover a vascular phantom that represents the vasculature of the subject; forming a plaque mold representing a plaque having dimensions based on the imaging data of the vasculature of the subject; infusing the plaque mold with a plaque component; freezing the plaque component; removing the plaque component from the plaque mold; and attaching the plaque component to the vascular phantom that represents the vasculature of the subject.

2. The method of fabricating a vascular phantom of claim 1, wherein said plaque represents one or more of a hemorrhage, a lipid core, and a fibrous cap.

3. The method of fabricating a vascular phantom of claim 2, wherein said one or more of the hemorrhage, the lipid core, and the fibrous cap comprises respective amounts of a T1 modifier and a T2 modifier.

4. The method of fabricating a vascular phantom of claim 1, wherein said step of attaching the plaque to the vascular phantom includes by coating a layer of adhesive on one or both of the shaped plaque and the vascular replica and performing a curing process.

5. The method of fabricating a vascular phantom of claim 1, wherein plaque component can comprise T1 and T2 modifiers, water, agarose, and carrageenan.

\* \* \* \* \*